United States Patent
Sugimoto et al.

(10) Patent No.: US 9,486,549 B2
(45) Date of Patent: Nov. 8, 2016

(54) AIR CLEANER FOR VEHICLE

(75) Inventors: Kazuhiro Sugimoto, Susono (JP);
Takashi Watanabe, Gotenba (JP)

(73) Assignee: Toyota Jidosha Kabushiki Kaisha,
Toyota-shi, Aichi-ken (JP)

( * ) Notice: Subject to any disclaimer, the term of this patent is extended or adjusted under 35 U.S.C. 154(b) by 489 days.

(21) Appl. No.: 14/004,441

(22) PCT Filed: Mar. 31, 2011

(86) PCT No.: PCT/JP2011/058192
§ 371 (c)(1),
(2), (4) Date: Sep. 11, 2013

(87) PCT Pub. No.: WO2012/131968
PCT Pub. Date: Oct. 4, 2012

(65) Prior Publication Data
US 2014/0010714 A1    Jan. 9, 2014

(51) Int. Cl.
| *A61L 9/00* | (2006.01) |
| *B01D 53/86* | (2006.01) |
| *F02M 27/02* | (2006.01) |
| *F02M 35/02* | (2006.01) |
| *F02M 35/16* | (2006.01) |
| *B01J 21/18* | (2006.01) |
| *B01J 23/38* | (2006.01) |
| *B01J 29/04* | (2006.01) |

(52) U.S. Cl.
CPC .............. *A61L 9/00* (2013.01); *B01D 53/8675* (2013.01); *F02M 27/02* (2013.01); *F02M 35/0218* (2013.01); *F02M 35/161* (2013.01); B01D 2253/102 (2013.01); B01D 2255/705 (2013.01); B01D 2257/106 (2013.01); B01D 2259/4566 (2013.01); *B01J 21/18* (2013.01); *B01J 23/38* (2013.01); *B01J 29/04* (2013.01)

(58) Field of Classification Search
CPC ................... B01D 53/8675; B01D 2257/106; B01D 2259/4566; F02M 27/02; B01J 23/38–23/52; A61L 9/00
See application file for complete search history.

(56) References Cited

U.S. PATENT DOCUMENTS 5,212,140 A * 5/1993 Yoshimoto ......... B01D 53/8675
423/219

FOREIGN PATENT DOCUMENTS

| EP | 2 689 823 | 1/2014 |
| JP | 2002-514966 | 5/2002 |
| WO | WO 96/22146 | 7/1996 |
| WO | WO 2012/127643 A1 | 9/2012 |

* cited by examiner

*Primary Examiner* — Timothy Cleveland
(74) *Attorney, Agent, or Firm* — Finnegan, Henderson, Farabow, Garrett & Dunner, LLP

(57) ABSTRACT

The present invention relates to an air cleaner for a vehicle. It is an object to provide a DOR system which can favorably suppress deterioration of a function of an ozone purifier containing ozone purifying catalyst and activated carbon. A core part of a radiator 14 includes a fin 20, an activated carbon layer 22, and an ozone purifying catalyst layer 24. The activated carbon layer 22 is made of activated carbon and a binder A for bonding the fin 20 and the activated carbon. The ozone purifying catalyst layer 24 is made of an organometallic complex and a binder B bonding the activated carbon layer 22 and the organometallic complex. The binder B used for the ozone purifying catalyst layer 24 has a larger specific surface area than that of the binder A used for the activated carbon layer 22.

3 Claims, 7 Drawing Sheets

Fig.7
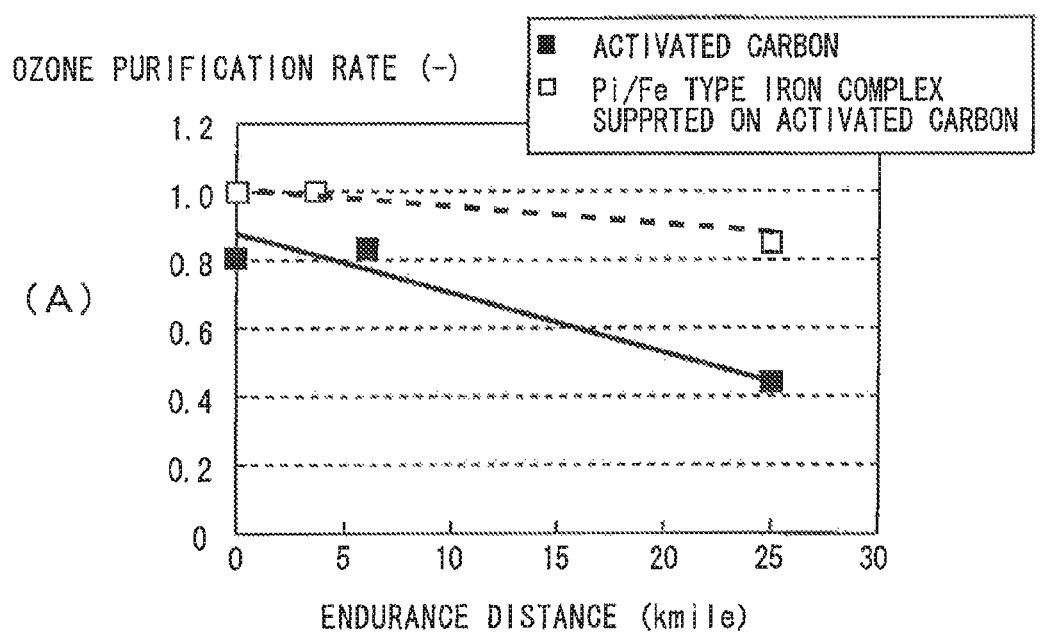
(A)
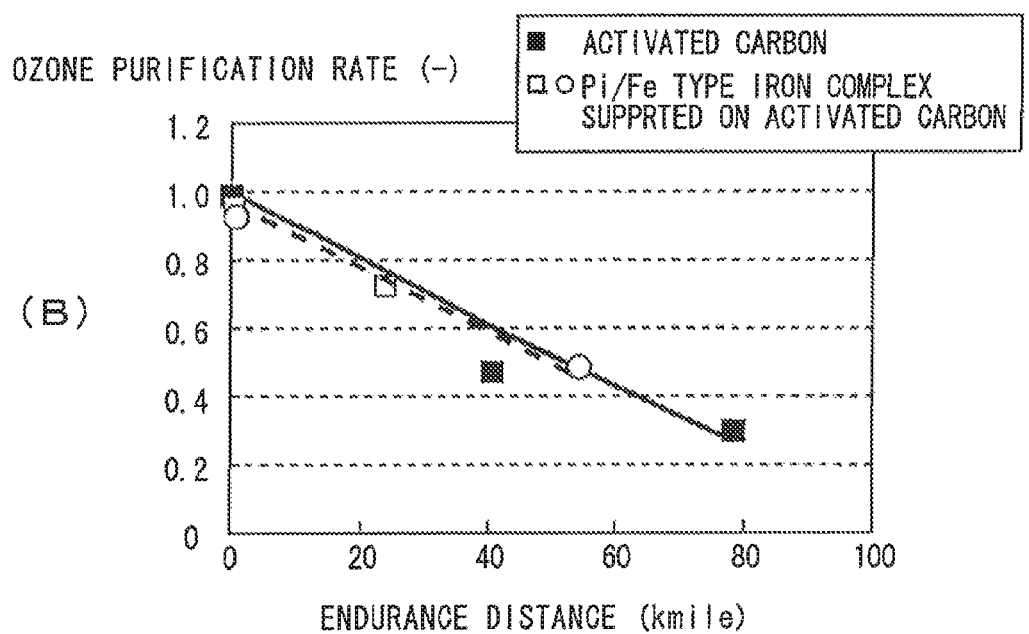
(B)

AIR CLEANER FOR VEHICLE

TECHNICAL FIELD

The present invention relates to an air cleaner for a vehicle, and more particularly, to an air cleaner for a vehicle capable of purifying ozone in air.

BACKGROUND ART

Ozone, which causes photochemical smog, is produced by a photochemical reaction of HC and NOx contained in exhaust gases from automobiles and factories. Therefore, reducing the amount of HC and NOx emissions from automobiles is an efficient way to suppress the production of ozone and prevent the occurrence of photochemical smog. Also, purifying ozone in the air directly can be one way to prevent the occurrence of photochemical smog. By purifying ozone as a product while reducing the amount of emissions of HC and NOx as reactants, the occurrence of photochemical smog can be prevented more effectively. Thus, an automobile including an air cleaner for a vehicle capable of directly purifying ozone in air has been put into practical use in some places including California in the United States of America. Such a cleaner is called a DOR (Direct Ozone Reduction) system.

For example, Patent Literature 1 discloses a DOR system in which a vehicle component such as a radiator carries a metal oxide such as manganese dioxide. The radiator is disposed at such a position as to be exposed to air during travel of a vehicle, and the manganese dioxide has a function of converting ozone contained in the air into other elements such as oxygen and purifying the ozone. Thus, according to the DOR system disclosed in Patent Literature 1, ozone in air can be directly purified while the vehicle travels is moving.

CITATION LIST

Patent Literature

Patent Literature 1: National Publication of International Patent Application No, 2002-514966

SUMMARY OF INVENTION

It has been known that not only metal oxide such as manganese dioxide but also activated carbon has a function of purifying ozone. Since the activated carbon has the function of purifying ozone as well as the metal oxide and is available at moderate price, it has been expected to be used as an alternative to the metal oxide. The activated carbon can purify ozone at ambient temperature (25° C.) and thus has an advantage over the metal oxide which purifies ozone at a higher temperature than the ambient temperature. However, there is a problem that when the activated carbon is used as an ozone purifier, its ozone purifying function is easily deteriorated.

The reason why the ozone purifying function of the activated carbon is easily deteriorated lies in how the function works. More specifically, active oxygen may be produced in addition to oxygen when the activated carbon dissolves ozone. Since the active oxygen has stronger oxidizing power than the ozone, it easily reacts with the activated carbon to oxidize it, thereby causing deterioration. Accordingly, when the activated carbon is simply applied to the DOR system, a vehicle component carrying it needs to be exchanged frequently. Thus, it is not practical.

In this regard, the inventors have found that a catalyst having a function of purifying ozone (hereinafter referred to as "ozone purifying catalyst") exists other than the metal oxide or the activated carbon, and the deterioration of the activated carbon may be suppressed by using the ozone purifying catalyst and the activated carbon at the same time as an ozone purifier. However, even when such an ozone purifier is used, the deterioration of the activated carbon may be still insufficient. Thus, further improvement is required.

The present invention, has been made in view of the above-described circumstances. It is an object to provide a DOR system which favorably suppresses deterioration of a function of an ozone purifier containing ozone purifying catalyst and activated carbon.

Means for Solving the Problem

To achieve the above mentioned purpose, a first aspect of the present invention is an air cleaner for a vehicle, comprising:

a vehicle component arranged on a portion where an air flow passage is formed when a vehicle is traveling; and an ozone purifier being formed on a surface of the vehicle component and containing an ozone purifying catalyst capable of purifying ozone and activated carbon, wherein, when a volume ratio of the ozone purifying catalyst relative to the activated carbon is defined as a carrying ratio, the carrying ratio on an air contact surface of the ozone purifier is adjusted to be larger than the carrying ratio on a vehicle component contact surface of the ozone purifier.

A second aspect of the present invention is the cleaner according to the first aspect, wherein the ozone purifier further includes a plurality of binders having different specific surface areas, and the binder used on the air contact surface of the ozone purifier has a larger specific surface area than that on the vehicle component contact surface of the ozone purifier.

A third aspect of the present invention is the cleaner according to the first or the second aspect, wherein the ozone purifier is composed of an air contact surface layer and a vehicle component contact surface layer, and the ozone purifying catalyst and a first binder are used for the air contact surface layer and the activated carbon and a second binder having a smaller specific surface area than the first binder are used for the vehicle component contact surface layer.

Advantageous Effects of Invention

The probability that air is contacted with activated carbon correlates with a degree of reduction of an ozone purification rate of the activated carbon. More specifically, the degree of reduction is increased when the probability that the air is contacted with the activated carbon is increased, and the degree of reduction is reduced when the probability is reduced. According to the first aspect of the present invention, the carrying ratio on the air contact surface of the ozone purifier is adjusted to be larger than the carrying ratio on the vehicle component contact surface of the ozone purifier. Therefore, the volume ratio of the activated carbon can be reduced on the air contact surface where the ozone concentration is high. Thus, the probability that the air is contacted with the activated carbon can be reduced and the degree of reduction of the ozone purification rate of the activated carbon can be reduced.

Also, the probability that the air is contacted with the ozone purifying catalyst correlates with the wind velocity of the air passing the ozone purifier containing the ozone purifying catalyst. More specifically, the probability that the air is contacted with the ozone purifying catalyst is reduced when the wind velocity is fast, and the probability is increased when the wind velocity is slow. Also, the wind velocity of the air correlates with the ease of desorption of ozone molecules coordinated onto the ozone purifying catalyst. More specifically, the ozone molecules are easily desorbed when the wind velocity is fast, and the ozone molecules are hardly desorbed when the wind velocity is slow. According to the first aspect of the present invention, the carrying ratio on the air contact surface of the ozone purifier is adjusted to be larger than the carrying ratio on the vehicle component contact surface of the ozone purifier. Thus, the probability that the air is contacted with the ozone purifying catalyst can be increased. In other words, the same condition as that when the wind velocity is slow can be provided on the air contact surface. Thus, the desorption of the ozone molecules from the ozone purifying catalyst can be suppressed and therefore the ozone purifying function of the ozone purifying catalyst can be efficiently utilized.

According to the second aspect of the present invention, the binder used on the air contact surface of the ozone purifier has a larger specific surface area than that on the vehicle component contact surface of the ozone purifier. Therefore, the probability that the air is contacted with the ozone purifying catalyst on the air contact surface can be increased, and the probability that the air is contacted with the activated carbon on the vehicle component contact surface can be reduced. The degree of reduction of the ozone purification rate of the activated carbon can be reduced while the ozone purifying function of the ozone purifying catalyst is effectively utilized. Thus, the life of the ozone purifier can be extended.

According to the third aspect of the present invention, the probability that the air is contacted with the ozone purifying catalyst on the air contact surface layer can be increased and thus the probability that the air is contacted with the activated carbon on the vehicle component contact surface layer can be reduced. The degree of reduction of the ozone purification rate of the activated carbon on the vehicle component contact surface layer can be reduced while the ozone purifying function of the ozone purifying catalyst is effectively utilized on the air contact surface layer. Thus, the life of the ozone purifier can be extended.

BRIEF DESCRIPTION OF DRAWINGS

FIG. 7 shows data of results of an ozone purification endurance test.

DESCRIPTION OF EMBODIMENT

[Structure of Vehicular Air Cleaner]

Figure 1:
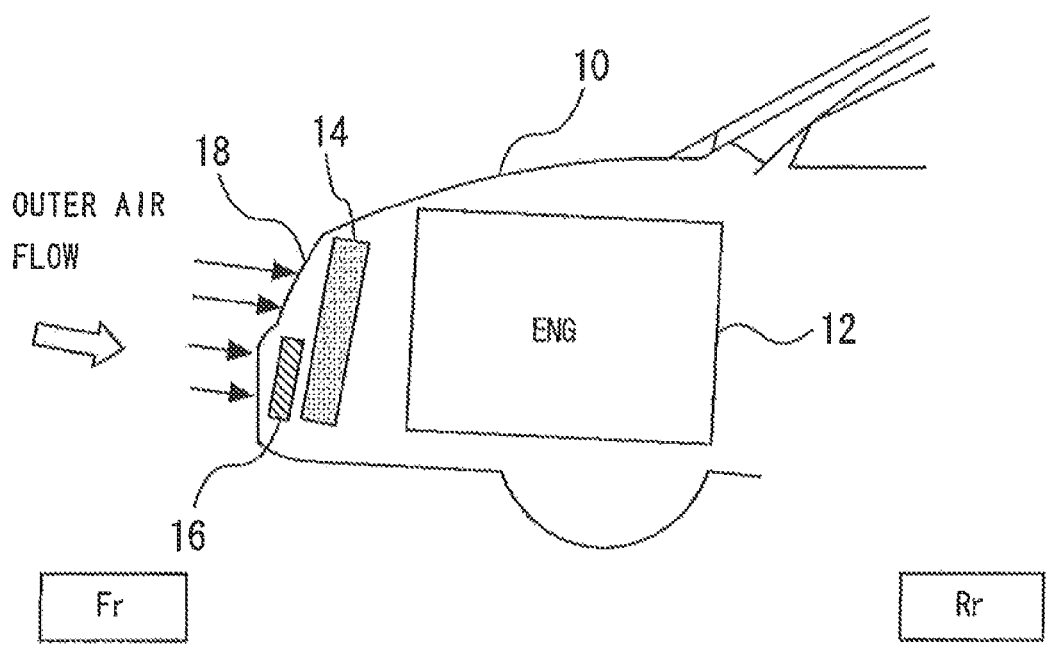
FIG. 1 is a schematic view showing a structure of a vehicle 10 on which an air cleaner for a vehicle according to an embodiment is applied.

An embodiment of the present invention will be explained below with reference to FIGS. 1 to 7. FIG. 1 is a schematic view showing a structure of a vehicle on which an air cleaner according to the embodiment is mounted. The vehicle 10 includes an internal combustion engine 12 serving as a power unit. Exhaust gas discharged from the internal combustion engine 12 contains HC and NOx. Ozone is produced by a photochemical reaction between HC and NOx as reactants. Therefore, when the air cleaner is mounted on the vehicle 10 including the internal combustion 12, the ozone is purified while the vehicle 10 is moving. And thus, the damage to the environment caused due to the vehicle 10 can be reduced.

In the vehicle 10, a radiator 14 for cooling coolant water circulating through the internal combustion engine 12 is arranged on the front side of the internal combustion engine 12. A condenser 16 of an air conditioner is mounted on the front side of the radiator 14. As shown by arrows in FIG. 1, air is taken in through a bumper grill 18 arranged on a front surface of the vehicle 10 during travel of the vehicle 10 and the taken in air is delivered through the condenser 16 and the radiator 14 in this order to be discharged to the rear side.

Figure 2:
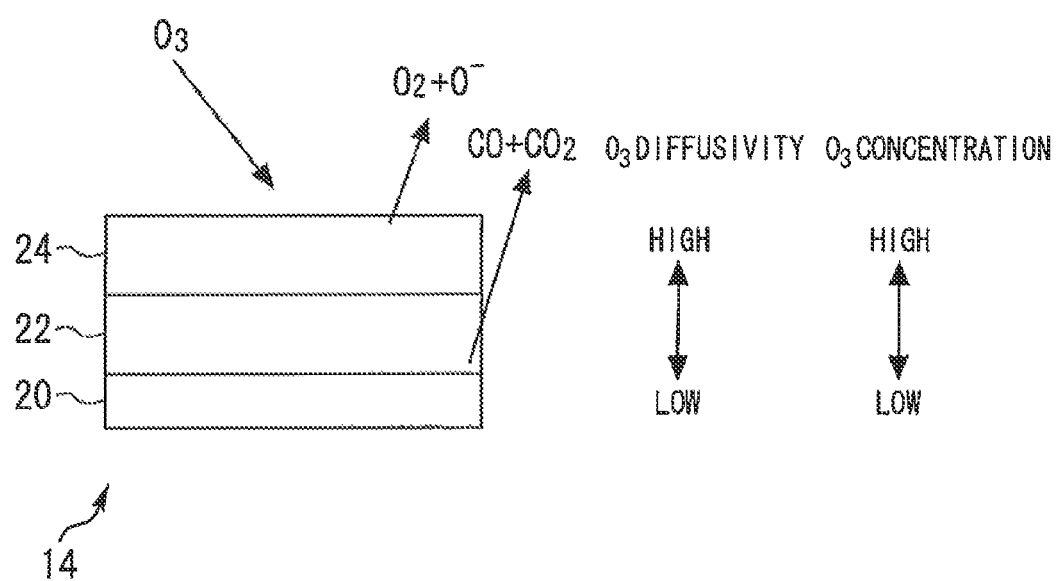
FIG. 2 is a cross-sectional view showing the core part of the radiator 14.

Next, a detailed structure of a core part of the radiator 14 will be explained with reference to FIG. 2. FIG. 2 is a cross-sectional view showing the core part of the radiator 14. As shown in FIG. 2, the core part of the radiator 14 includes a fin 20, an activated carbon layer 22, and an ozone purifying catalyst layer 24. The fin 20 is made of aluminum alloy or the like which has excellent thermal conductivity. The activated carbon layer 22 is made of activated carbon and a binder A bonding the fin 20 and the activated carbon. Also, the ozone purifying catalyst layer 24 is made of an organometallic complex composed of manganese, iron, cobalt, nickel, copper, ruthenium, rhodium, or palladium as a center metal, and a binder B bonding the activated carbon layer 22 and the organometallic complex.

[Characteristics of Embodiment]

Figure 3:
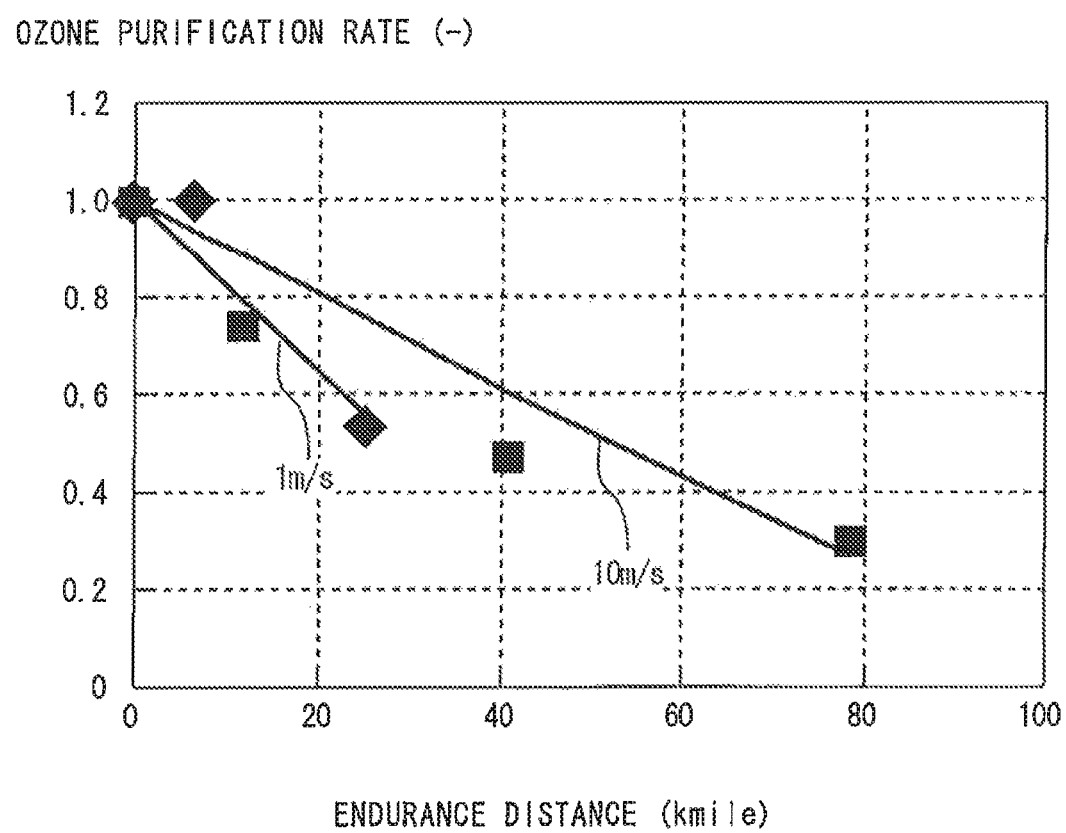
FIG. 3 shows data of results of an ozone purification endurance test.

FIG. 3 shows data of results of an ozone purification endurance test. In FIG. 3, the horizontal axis represents an endurance distance (in kilomiles) and the vertical axis represents a relative value based on an ozone purification rate at an initial state (when the endurance distance is 0 kilomiles). The data shown in FIG. 3 is obtained by preparing two activated carbons of equivalent sizes and specific surface areas, and then measuring the rear side ozone concentration of the two activated carbons when a gas containing ozone having a predetermined concentration passes through these activated carbons from the front side toward the rear side at different velocities (wind velocities of 1 m/s and 10 m/s).

As shown in FIG. 3, the ozone purification rate of the activated carbon is reduced as the endurance distance becomes longer. Also, as shown in FIG. 3, the degree of reduction of the ozone purification rate of the activated carbon is changed depending on the wind velocity of the passing gas containing ozone. More specifically, in the case where the gas containing the ozone passes at the wind velocity of 1 m/s, the ozone purification rate goes down by half from the ozone purification rate at the initial state when the endurance distance is approximately 30 kilomiles. In the case where the gas containing the ozone passes at the wind velocity of 10 m/s, the ozone purification rate remains at about 70% or more of the ozone purification rate at the initial state when the endurance distance is approximately 30 kilomiles, and then goes down by half from the purification rate at the initial state when the endurance distance is approximately 60 kilomiles. In other words, the degree of reduction of the ozone purification rate is smaller when the gas passes at high speed (wind velocity of 10 m/s) as compared to when the gas passes at low speed (wind velocity of 1 m/s).

Figure 4:
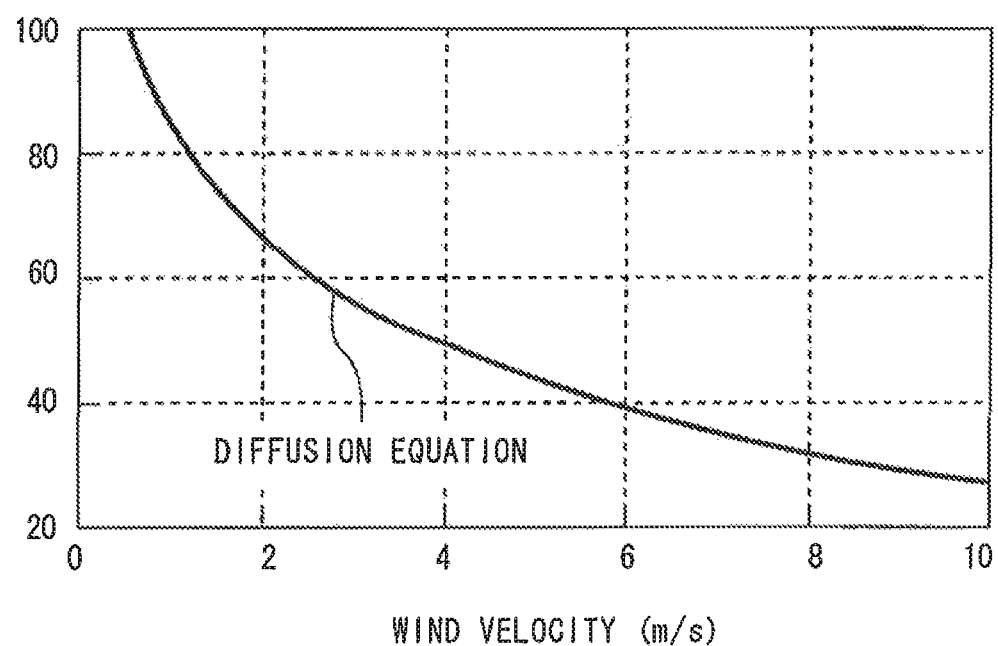
FIG. 4 is a graph showing a relationship between the wind velocity of a gas passing through the radiator and the probability that the gas is contacted with the radiator.

FIG. 4 is a graph showing a relationship between the wind velocity of a gas passing through a radiator and the probability that the gas is contacted with the radiator (hereinafter referred to as "gas contact probability"). This graph is provided by applying the Gormley-Kennedy diffusion equation to a model of an aluminum honeycomb radiator. As shown in FIG. 4, the probability that the gas is contacted with the radiator is approximately 100% when the wind velocity is approximately 1 m/s. Also, the probability that the gas is contacted with the radiator is decreased to approximately 10% when the wind velocity is approximately 10 m/s. In other words, the probability that the gas is contacted with the radiator is high when the wind velocity is slow, and is gradually lowered as the wind velocity is faster.

From the graphs shown in FIGS. 3 and 4, it is found that the ozone purification rate of the activated carbon and the gas contact probability correlate with each other. It is found from the graph shown in FIG. 4 that the gas contact probability is higher as the wind velocity is slower and the gas contact probability is lower as the wind velocity is faster. Also, it is found from the graph shown in FIG. 3 that the degree of reduction of the ozone purification rate is larger as the wind velocity is slower and the degree of reduction of the ozone purification rate is smaller as the wind velocity is faster. Accordingly, from the graphs in FIGS. 3 and 4, it is obvious that the degree of reduction of the ozone purification rate of the activated carbon is greater as the gas contact probability is higher and the degree of reduction of the ozone purification rate of the activated carbon is lesser as the gas contact probability is lower.

The inventors estimate that the reason why the ozone purification rate of the activated carbon and the gas contact probability correlate with each other as described above is because of an ozonolysis mechanism of the activated carbon and aging of the inner structure of the activated carbon. First, the ozonolysis mechanism of the activated carbon will be explained below. The activated carbon has countless fine pores extend from its surface toward its inner side. When ozone molecules enter into such fine pores, electrons are provided from the activated carbon and activation energy of an ozonolysis reaction is reduced. Consequently, ozone is converted into oxygen and active oxygen. The ozonolysis reaction of the activated carbon is represented specifically by the following expressions (1) and (2).

$$O_3 \rightarrow O_3^-$$ (1)

$$O_2^- \rightarrow O_2 + O^-$$ (2)

Next, the aging of the inner structure of the activated carbon will be explained below. The active oxygen ($O^-$) produced by the ozonolysis reaction of the activated carbon serves as an oxidant of the activated carbon. Since this active oxygen has strong oxidizing power, the activated carbon is oxidized when the active oxygen enter into the fine pores of the activated carbon. Thus, the ozone purifying function of the activated carbon may disappear. The oxidation reaction of the activated carbon caused by the active oxygen is represented specifically by the following expressions (3) and (4), $$C + O \rightarrow CO$$ (3)

$$C + 2O \rightarrow CO_2$$ (4)

Incidentally, the organometallic complex has an ozone purifying function as well as the activated carbon. The ozonolysis reaction of the organometallic complex is represented specifically by the following expressions (5) and (6).

$$O_3 \rightarrow O_3^-$$ (5)

$$O_3^- \rightarrow O_2 + O^-$$ (6)

The reaction represented by the expressions (5) and (6) proceeds on the center metal of the organometallic complex, and is the same as the reaction represented by the expressions (1) and (2). Thus, when the organometallic complex is used with the activated carbon, the gas contact probability that the gas is contacted with the activated carbon is considered to be relatively reduced.

Also, the organometallic complex can convert the active oxygen produced by the ozonolysis reaction of the activated carbon into oxygen. The reaction of the active oxygen caused specifically by the organometallic complex is represented by the following expression (7).

$$O^- + O_3 \rightarrow 2O_2$$ (7)

The reaction represented by the expression (7) proceeds on the center metal of the organometallic complex as well as the reaction represented by the expressions (5) and (6). For this reaction, $O_3^-$ and $O^-$ produced by the reaction represented by the expressions (1) and (2) as well as the reaction represented by the expressions (5) and (6) may react. Thus, when the organometallic complex is used with the activated carbon, the oxidation reaction (the reaction represented by the expressions (3) and (4)) of the activated carbon caused by the active oxygen is considered to be suppressed.

Figure 5:
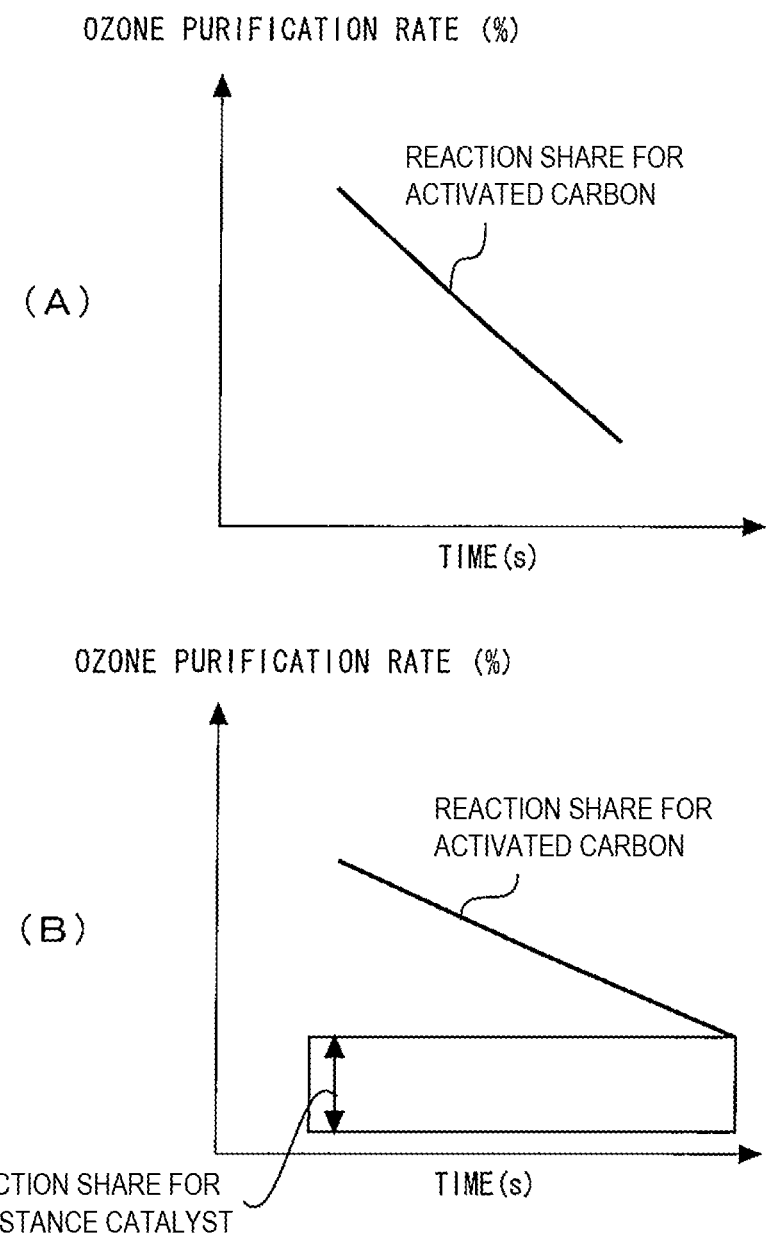
FIG. 5 shows an anticipated aging of a ozone purification rate of an ozone purifier utilizing an organometallic complex and activated carbon.

FIG. 5 shows the anticipated aging of the ozone purification rate of the ozone purifier utilizing the organometallic complex and the activated carbon. As described above, when the organometallic complex is used with the activated carbon, the gas contact probability that the gas is contacted with the activated carbon can be relatively reduced and thus the oxidation reaction of the activated carbon caused by the active oxygen can be suppressed. Thus, as shown in FIG. 5, when an assistance catalyst (i.e., organometallic complex) is used with the activated carbon (FIG. 5(B)), it can be said that the life of the ozone purifier is extended as compared when the activated carbon is used independently (FIG. 5(A)).

Figure 6:
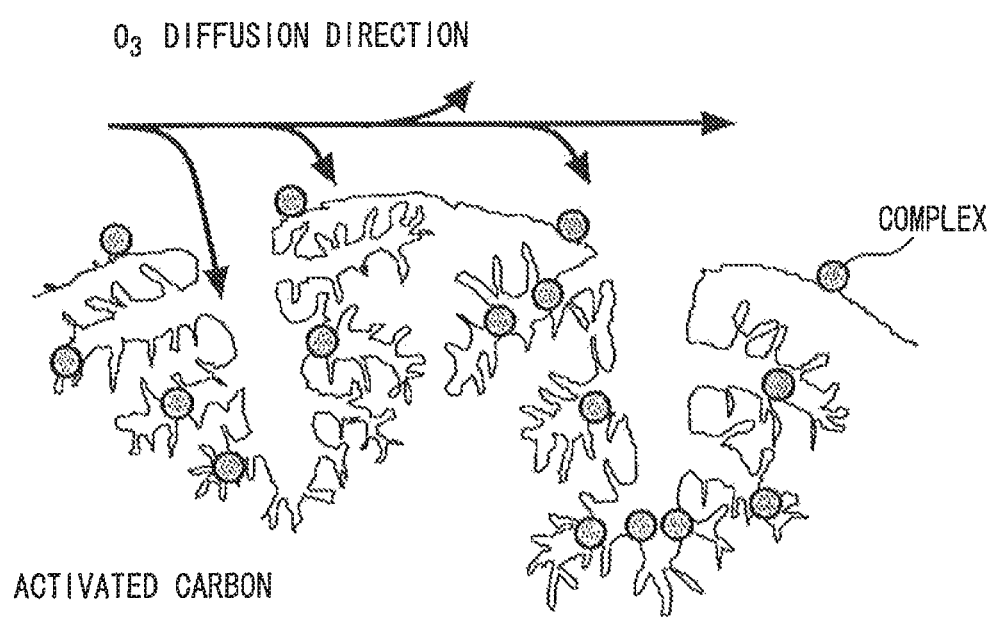
FIG. 6 shows an inner structure of activated carbon on which the organic complex is dispersed and supported.

However, even when the organometallic complex is used with the activated carbon, progression of deterioration of the ozone purifying function of the ozone purifier cannot be sufficiently suppressed under the condition that the wind velocity is fast. FIG. 6 shows the inner structure of the activated carbon on which the organic complex is dispersed and supported. As shown by arrows in FIG. 6, the ozone molecules are delivered on the surface of the ozone purifier. Then, the ozone molecules enter into the fine pores of the activated carbon, or coordinated onto the center metal of the organometallic complex. However, under the condition that the wind velocity is fast, a desorption phenomenon, in which the ozone molecules entering into the fine pores are scraped out before purification or are peeled from the organometallic complex, may occur. On the other hand, under the condition that the wind velocity is slow, the probability that the desorption phenomenon is occurred is reduced.

FIG. 7 shows data of results of an ozone purification endurance test. In FIG. 7, the horizontal axis represents an endurance distance (in kilomiles) and the vertical axis represents a relative value based on an ozone purification rate at an initial state (when the endurance distance is 0 kilomiles). The data shown in FIG. 7 is obtained by preparing two activated carbons on which picket-fence porphyrin complex (the center metal is iron) is supported (their sizes and specific surface areas are equivalent), and then measuring the rear side ozone concentration of the two activated carbons when a gas containing ozone having a predetermined concentration passes through these activated carbons from the front side toward the rear side at different velocities (wind velocities of 1 m/s and 10 m/s).

FIG. 7 shows the data shown in FIG. 3 for comparison with the data of the activated carbons on which the above-described complex is dispersed and supported. Incidentally, the data shown in FIG. 3 is indicated as the relative value based on the ozone purification rate at the initial state of the activated carbon on which the complex is dispersed and supported. FIG. 7(A) is data obtained when the gas passes at the wind velocity of 1 m/s, and FIG. 7(B) is data obtained when the gas passes at the wind velocity of 10 m/s. From FIG. 7(A), it is found that reduction of the ozone purification rate in the activated carbon on which the above-described complex is dispersed and supported is suppressed as compared to that in the activated carbon shown in FIG. 3. It can be said that this data shown in FIG. 7(A) supports the fact that the ozone molecules enter into the fine pores of the activated carbon, coordinated onto the organometallic complex as well, and purified without desorption. On the other hand, it is found from FIG. 7(B) that the degree of reduction of the ozone purification rate in the activated carbon on which the above-described complex is dispersed and supported is approximately the same as that in the activated shown in FIG. 3. In other words, the data shown in FIG. 7(A) supports the fact that the ozone molecules coordinated onto the organometallic complex are desorbed before the purification while the ozone molecules entering into the fine pores of the activated carbon are quickly purified.

As described above, in the organometallic complex, the degree of the ozone purification is different depending on the difference between the reaction speed of the ozone purification reaction and the desorption speed of the ozone molecules. Thus, in this embodiment, the binder B having a larger specific surface area than that of the binder A forming the activated carbon layer 22 is used for the ozone purifying catalyst layer 24. In general, diffusivity of gas is increased in a substance having a large specific surface area. Accordingly, when the binder B having the larger specific surface area than that of the binder A is used for the ozone purifying catalyst layer 24, the probability that air is contacted with the organometallic complex in the ozone purifying catalyst layer 24 can be increased. Thus, the condition that the wind velocity is slow can be provided and therefore the desorption of the ozone molecules from the organometallic complex before the purification can be suppressed.

On the other hand, diffusivity of gas is reduced in a substance having a small specific surface area. Thus, when the binder A having a smaller specific surface area than that of the binder B is used for the activated carbon layer 22, the probability that air is contacted with the activated carbon in the activated carbon layer 22 can be reduced. As already explained with reference to FIGS. 3 and 4, when the gas contact probability is reduced, the degree of reduction of the ozone purification rate of the activated carbon is reduced.

Thus, the condition that the wind velocity is fast can be provided in the activated carbon layer 22, and therefore the degree of reduction of the ozone purification rate of the activated carbon can be reduced.

From the above, in this embodiment, the desorption of the ozone molecules from the organometallic complex in the ozone purifying catalyst layer 24 can be suppressed and the degree of reduction of the ozone purification rate in the activated carbon layer 22 can be reduced. Thus, the life of the ozone purifier can be extended while the ozone purifying function of the organometallic complex is effectively utilized.

Although the binder A is used for the activated carbon layer 22 and the binder B is used for the ozone purifying catalyst layer 24 respectively in the embodiment described above, a part of the binder A may be used for the ozone purifying catalyst layer 24 and a part of the binder B may be used for the activated carbon layer 21. Also, although two typos of binders A and B having different specific surface areas are used in the embodiment, more than two types of binders may be used. Various binders can be selected as long as the probability that air is contacted with the organometallic complex of the ozone purifying catalyst layer 24 can be increased and the probability that the air is contacted with the activated carbon of the activated carbon layer 22 can be reduced.

Although the ozone purifier is made of two layers of the activated carbon layer 22 and the ozone purifying catalyst layer 24 in the embodiment described above, more than two layers may be used. For example, three layers may be used by disposing an intermediate layer provided by mixing the activated carbon and the ozone purifying catalyst between the activated carbon layer 22 and the ozone purifying catalyst layer 24. Various modifications to the structure of layers in the ozone purifier can be made as long as the probability that air is contacted with the organometallic complex of the ozone purifying catalyst layer 24 can be increased and the probability that the air is contacted with the activated carbon of the activated carbon layer 22 can be reduced.

Although the organometallic complex is used for the ozone purifying catalyst layer 24 in the embodiment described above, a metal complex may be used instead of the organometallic complex. Alternatively, the ozone purifying catalyst layer 24 may be coated with palladium, silver, platinum, gold, or zeolite. These alternative elements have an ozone purifying function and exhibit resistance to the active oxygen as well as the organometallic complex. The metal complex which can be used as the alternative element may be any one of the metals described as the center metal of the organometallic complex. Incidentally, two types or more of the alternative elements may be used in combination. Alternatively, they may be used with the organometallic complex.

DESCRIPTION OF REFERENCE NUMERALS 10 vehicle
12 engine
14 radiator
16 capacitor
18 bumper grill
20 fin
22 activated carbon layer (vehicle component contact surface layer)
24 ozone purifying catalyst layer (air contact surface layer)

The invention claimed is:

1. An air cleaner for a vehicle, comprising:
a vehicle component arranged on a portion where an air flow passage is formed when a vehicle is traveling; and
an ozone purifier being formed on a surface of the vehicle component and containing an ozone purifying catalyst capable of purifying ozone and an activated carbon capable of purifying ozone, wherein,
a volume ratio of the ozone purifying catalyst to the activated carbon is greater on an air contact surface of the ozone purifier than on a vehicle component contact surface of the ozone purifier.

2. The cleaner according to claim 1, wherein the ozone purifier further includes a plurality of binders having different specific surface areas, and the binder used on the air contact surface of the ozone purifier has a larger specific surface area than that on the vehicle component contact surface of the ozone purifier.

3. The cleaner according to claim 1, wherein the ozone purifier is composed of a surface layer formed on the air contact surface and a surface layer formed on the vehicle component contact surface, and
the ozone purifying catalyst and a first binder are used for the surface layer formed on the air contact surface, and the activated carbon and a second binder having a smaller specific surface area than the first binder are used for the surface layer formed on the vehicle component contact surface.

* * * * *